United States Patent [19]

Elist

[11] Patent Number: 5,662,709

[45] Date of Patent: Sep. 2, 1997

[54] IMPLANT FOR IMPROVING THE SIZE AND SHAPE OF A TESTIS

[76] Inventor: James J. Elist, 9301 Wilshire Blvd., Suite 401, Beverly Hills, Calif. 90210

[21] Appl. No.: 647,298

[22] Filed: May 9, 1996

[51] Int. Cl.$^6$ ........................................................ A61F 2/02
[52] U.S. Cl. ............................................................. 623/11
[58] Field of Search ............................ 623/7, 8; 600/38–41

[56]  References Cited

U.S. PATENT DOCUMENTS 3,919,724   11/1975   Sanders et al. ............................ 623/8

*Primary Examiner*—David Isabella
*Assistant Examiner*—John M. Black
*Attorney, Agent, or Firm*—Gene Scott—Patent Law & Venture Group

[57]  ABSTRACT

An implant device is disclosed for expanding the girth of, and improving the appearance of a testis. A pair of soft, flexible bodies are implanted within the scrotum and joined to the testes. Each of the bodies and the testis to which it is attached, take the shape of a sphere. When implanted, the body covers a portion of the testis not including the testicular cord.

4 Claims, 1 Drawing Sheet

IMPLANT FOR IMPROVING THE SIZE AND SHAPE OF A TESTIS

FIELD OF THE INVENTION

This invention relates generally to implants in the human body and, more particularly, is directed towards an implant device for improving the size and shape of a testis.

BACKGROUND OF THE INVENTION

Every part of the human body is subject to deterioration, disease and damage. Losses in human form and function are generally the result. Medical materials and procedures, as ever, are providing remedies for the problems brought about by these losses. Today the art of medical materials implantation has been brought to a high level of success. Implants are being used for remedying a wide range of problems stemming from birth defects, to war and accident related malformations in many parts of the body. In the human male, the testes provides an important function in human reproduction. This important organ also is a primary sexual object in the art of lovemaking both as a stimulus to the female, as well as in building sexual confidence in the male. Should the scrotum appear mis-shapen, or smaller than average size, this fact may have an adverse effect on the male's ability to maintain a sexual relationship with a female. A remedy is not presently known or taught, in medicine.

Clearly, then, there is a need for a scrotal implant device that is primarily directed at increasing testis girth and improving its shape. Such a device would not impede testis function whatever. Further, such a device would have a smooth, natural look and feel. The present invention fulfills these needs and provides further related advantages.

SUMMARY OF THE INVENTION

The present invention is an implant device for expanding the girth and for providing a natural globular, firm, appearance and feel to the human testis. A pair of soft, flexible bodies are implanted within the scrotum and attached, one to each testis. The bodies are generally spherical in shape. When implanted, the body covers a portion of the existing testis and extends away from it. Together, the testis and body form a continuous spherical shape that provides for a change in size and shape so as to appear and feel more natural than the testis might be.

The structure of the present invention provides a spherically shaped thick wall having an aperture within it. The method of the present invention provides for attachment, with sutures, of the existing testis at the aperture in the spherical wall. As such, the present invention is well suited for male patients that suffer from small gonad size or from a gonad malformity. The present device further has a smooth, natural look and feel. Thus it is an object of the present invention to provide an implant to improve the size of an existing testis. It is a further object of the invention to provide such an implant that compliments the shape of the testis so as, together, to appear fully normal in size and shape. It is a final object of the present invention to provide a method of improving the size and shape of the male gonad. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
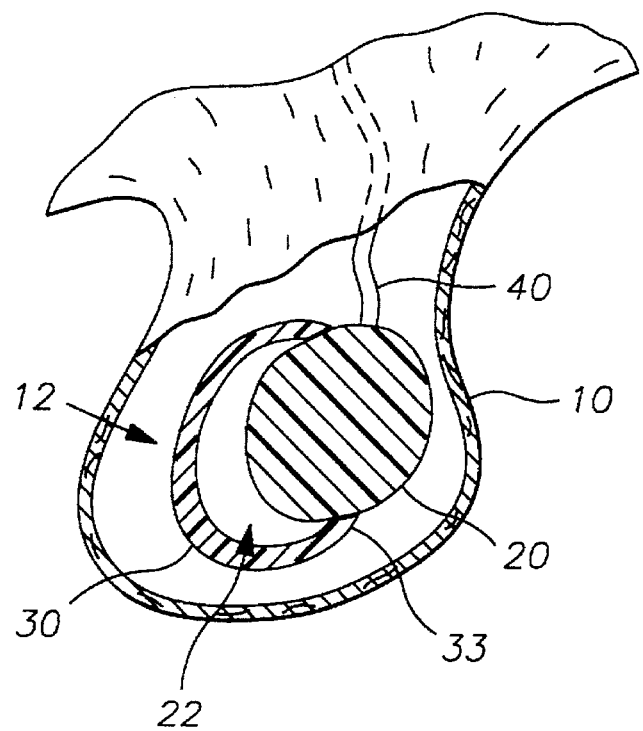
FIG. 1 is a side elevational view of a scrotum with a portion of the scrotum wall cut away to reveal a testis positioned so as to be partially enclosed within the spherical body of the invention; both the testis and the body being illustrated in cross section.
Figure 2:
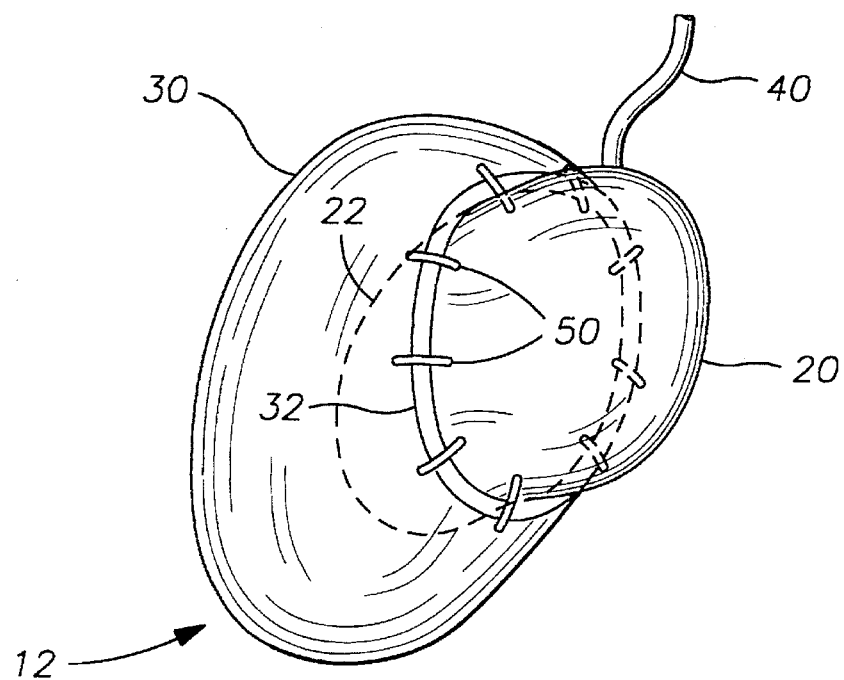
FIG. 2 is a perspective view of the testis as sutured to the body.

FIGS. 1 and 2 show an implant device for expanding the girth, and improving the shape of a testes 20. The device provides a soft, flexible and generally spherical, hollow, implantable body 12 for implanting within a scrotum 10. The body 12 provides a wall 30 having an aperture 32 for communication between the scrotum 10 generally, and the interior of the body 12. The aperture 32 provides and defines an aperture rim 33. The testis 20 is fixed at least partially within the aperture 32 of the body, and held in position against the aperture rim 33 by a means, preferably sutures 50, for attaching the testis 20 to the body 12. The testis 20 is positioned such that the testicular cord 40 is located external to the body 12. A portion 22 of the testes 20 is positioned within the wall 30. The portion 22 is defined by the aperture rim 33 as shown in FIG. 1. The device is formed of a physiologically acceptable implant material such as a silicone rubber. The body 12 is shaped so that the body 12 and testis 20, when joined together, are generally spherical in shape. To achieve this result, the body is preferably custom formed and shaped to meet the requirements of a particular patient.

The method of the invention improves the size and shape of the male gonad, and comprises the steps of providing an incision in the tunica vaginalis to expose the testes within, placing the generally spherical bodies 12 having complimentary shapes to each of the testis, around each of the testis 20, and suturing each one of the bodies 12 to the epididymis of one of the testis 20 so that the testis 20 extends from the aperture 32 in the body 12, the testicular cord 40 extending away from the body 12; and closing the incision.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. An implant device for improving the shape of, and expanding the girth of a testis, the device comprising:

a soft, flexible and generally spherical implantible body for implanting within a scrotum, the body providing a wall, defining an aperture in the wall and an aperture rim;

the aperture rim being of a size for fitting around a portion of the testis and for being attached thereto such that a testicular cord of the testis extends from the testis, and externally to the body, the body enclosing at least a portion of the testes.

2. The device of claim 1 wherein the device is formed of a physiologically acceptable implant material.

3. The device of claim 2 wherein the body is shaped so that the body and testis, when joined together, are generally spherical in shape.

4. A method of improving the size and shape of the male gonad, comprising the steps of:
   a) providing an incision in the tunica vaginalis to expose the testes within;
   b) placing a generally spherical body having a complimentary shape to each of testis, and made of a physiologically acceptable implant material, around each of the testis;
   c) suturing each one of the bodies to one of the testis so that the testis extends from an aperture in the body, the testicular cord extending away from the body; and
   d) closing the incision.

* * * * *